US007045656B2

(12) United States Patent
Gotteland et al.

(10) Patent No.: US 7,045,656 B2
(45) Date of Patent: May 16, 2006

(54) SELECTIVE SEPARATION OF IRON BY TREATMENT WITH AN ION-EXCHANGING RESIN COMPRISING DIPHOSPHONIC ACID GROUPS

(75) Inventors: Patrice Gotteland, Lyons (FR); Sébastien Logette, Lyons (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 10/846,591

(22) Filed: May 17, 2004

(65) Prior Publication Data

US 2004/0213718 A1     Oct. 28, 2004

Related U.S. Application Data

(62) Division of application No. 10/009,732, filed as application No. PCT/FR00/01587 on Jun. 8, 2000, now Pat. No. 6,872,369.

(30) Foreign Application Priority Data

Jun. 15, 1999   (FR) .................................. 99 07790

(51) Int. Cl.
   *C07C 51/245* (2006.01)
(52) U.S. Cl. .................. 562/528; 562/538; 562/590
(58) Field of Classification Search ................ None
   See application file for complete search history.

(56) References Cited

U.S. PATENT DOCUMENTS 3,965,164 A    6/1976 Blay
5,281,631 A    1/1994 Horwitz et al.
5,582,737 A   12/1996 Gula et al.
5,723,098 A *  3/1998 Salzburg et al. ............ 423/139
6,232,353 B1   5/2001 Alexandratos et al.
2003/0144555 A1* 7/2003 Lee et al. ................... 568/338

FOREIGN PATENT DOCUMENTS

EP          0 761 638         3/1997

OTHER PUBLICATIONS

Technical Data from <http://www.puroliteusa.com/ftp/ProductData/Chelation/S-940_0400.pdf.>, p. 1, last visited on Jun. 7, 2005.*
Chiarizia et al., "Diphonix resin: a review of its properties and applications," *Separation Science and Technology*, vol. 32, No. 1-4, pp. 1-35, 1997.
Abstract of SU 277766, Database WPI, Section CH, Week 197134, Derwent Publications Ltd., London, GB; AN 1971-55098S, no month, 1971.

* cited by examiner

*Primary Examiner*—Johann Richter
*Assistant Examiner*—Karl Puttlitz
(74) *Attorney, Agent, or Firm*—Buchanan Ingersoll, P.C.

(57) ABSTRACT

A process is described for recycling catalysts in the reaction for the oxidation of alcohols and/or ketones to carboxylic acids and more particularly the oxidation of cyclic alcohols and/or cyclic ketones to dicarboxylic acids, such as the oxidation of cyclohexanol and/or cyclohexanone to adipic acid. This process involves treating the solution comprising the oxidation catalyst, before it is recycled, with an ion-exchange resin which makes it possible to selectively separate the iron from the other metal elements, in particular from copper and from vanadium.

6 Claims, 3 Drawing Sheets

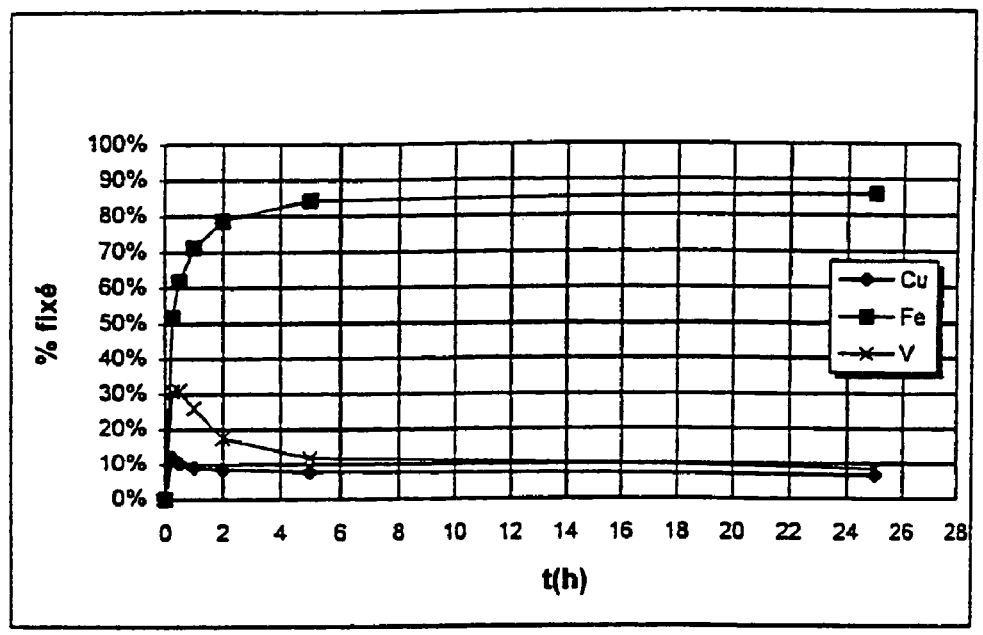
FIG. -1-
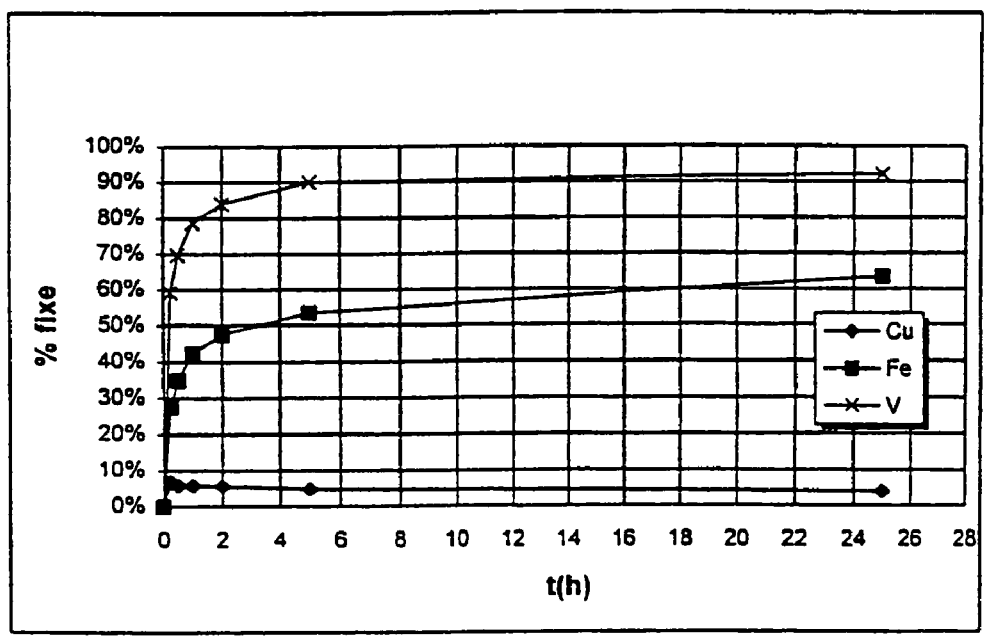
FIG.-2-

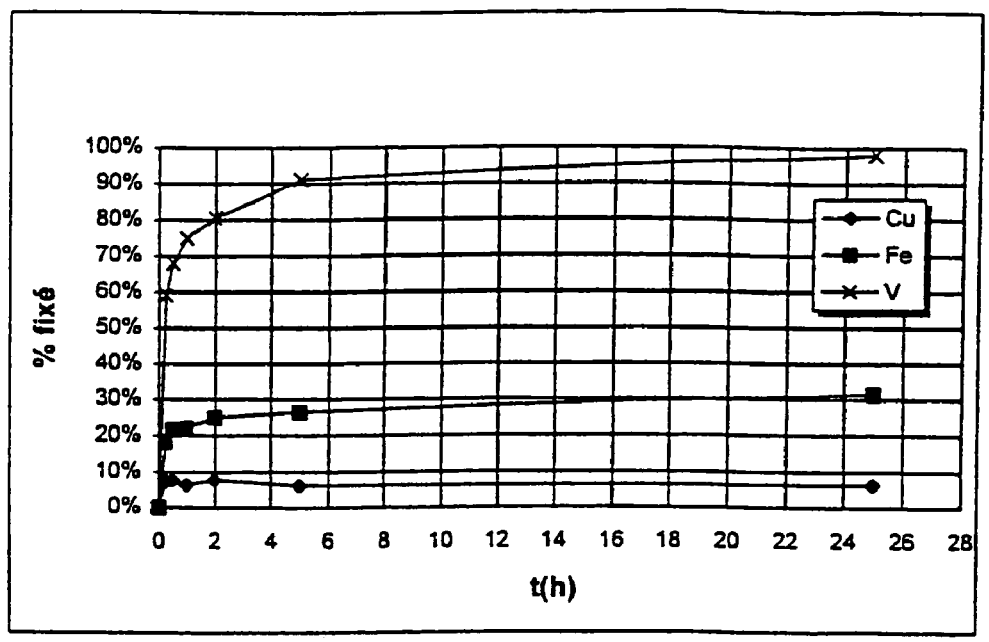
FIG.-3-
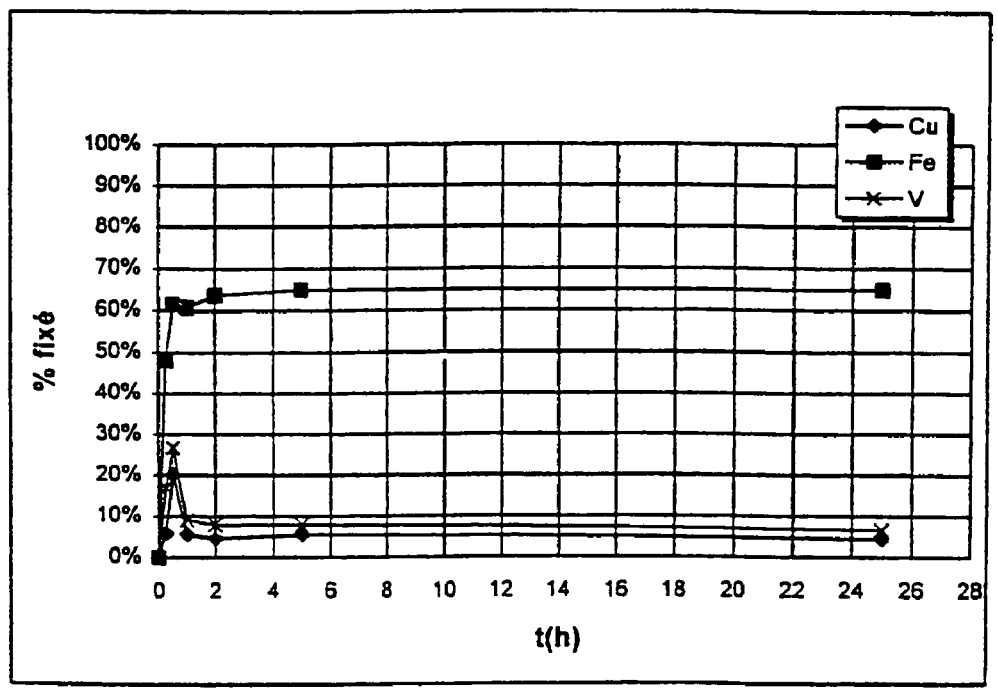
FIG. -4-

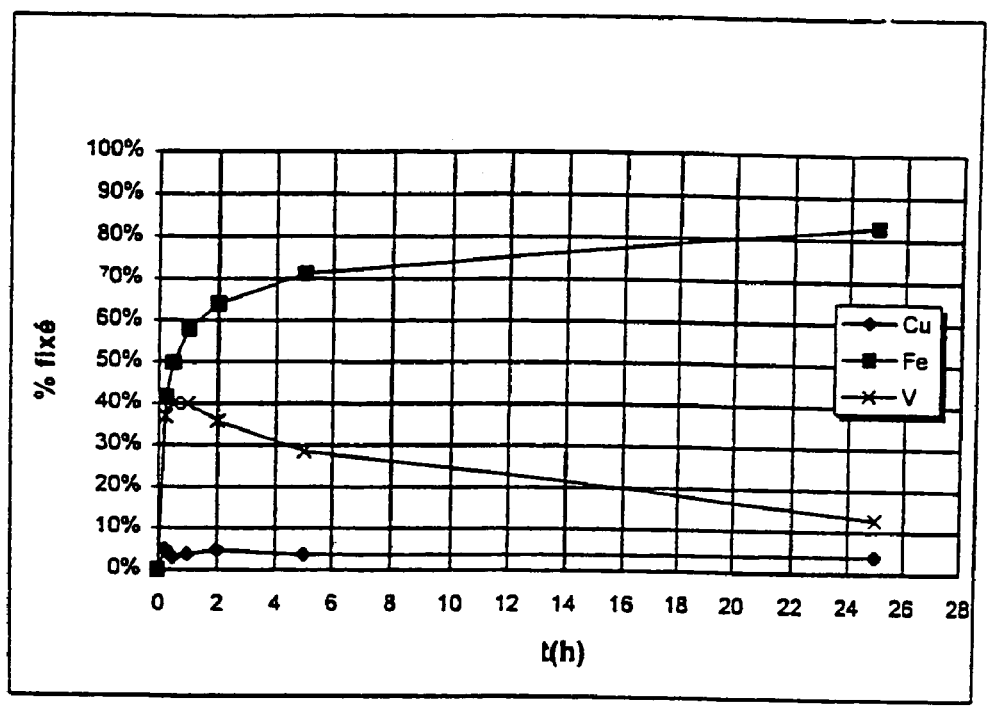
FIG. —5—
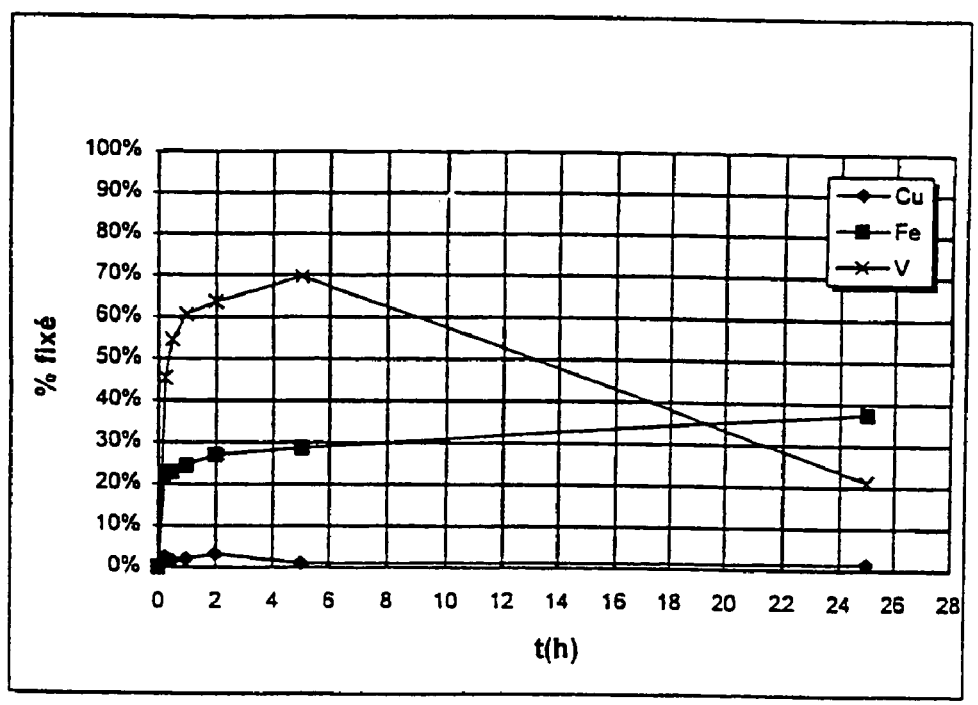
FIG. —6—

SELECTIVE SEPARATION OF IRON BY TREATMENT WITH AN ION-EXCHANGING RESIN COMPRISING DIPHOSPHONIC ACID GROUPS

CROSS-REFERENCE TO RELATED APPLICATIONS

This application is a divisional of U.S. application, Ser. No. 10/009,732, filed Apr. 23, 2002 now U.S. Pat. No. 6,872,369, which claims priority from French Application No. 99/07790, filed on Jun. 15, 1999, and PCT international application No. PCT/FR00/01587, filed on Jun. 8, 2000, the contents of which are incorporated herein.

BACKGROUND OF THE INVENTION

1. Field of the Invention

The invention relates to a process for selectively separating iron from other metal ions, in particular ions present in certain oxidation catalysts.

It also relates to a process for recycling catalysts in the reaction for the oxidation of alcohols and optionally ketones to carboxylic acids and more particularly the oxidation of cyclic alcohols and cyclic ketones to dicarboxylic acids, such as the oxidation of cyclohexanol and/or cyclohexanone to adipic acid.

2. Description of the Related Art

Thus, it is known to manufacture adipic acid by nitric oxidation of a mixture of cyclohexanol and cyclohexanone. This oxidation is generally carried out in the presence of a catalyst comprising vanadium and copper.

The solution recovered after separation of the dicarboxylic acids and in particular of adipic acid is treated in order to allow the catalyst to be recycled in the oxidation reaction.

Several processes for the treatment of this solution have been provided. For example, the metals present in the solution can be extracted by treatment with ion-exchange resins. The solution, purified of metals, comprises the byproducts from the synthesis of adipic acid, namely glutaric and succinic acids. Such a process is disclosed, for example, in U.S. Pat. No. 3,965,164.

However, this process does not allow iron ions, originating in particular from the corrosion of the plants, to be removed. Thus, the catalyst is enriched in iron at each recycling cycle. This enriching can decrease the efficiency of the catalyst or can also contaminate the adipic acid manufactured.

Several processes have been provided for at least partially removing the iron without loss of vanadium and of copper.

Other processes consist in selectively and differentially eluting the vanadium and the copper from the ion-exchange resin by using nitric acid solutions at a more or less high concentration or elution solutions comprising acids other than nitric acid or phosphonic acid (SU 690,320, U.S. Pat. No. 3,554,692).

However, these processes do not make possible selective removal of the iron without significant loss of vanadium or copper, in view of the ratio of very low concentration of iron with respect to the other two metal ions.

To overcome these disadvantages, European Patent Application No. 0,761,636 provides a process which consists in treating the eluate comprising the iron, copper and vanadium ions with a second ion-exchange resin comprising aminophosphoric groups.

Although improving the prior processes, this process does not make it possible to remove most of the iron ions without loss, in particular, of vanadium ions, which is highly prejudicial to the oxidation process. This is because these resins can have a satisfactory selectivity for iron with respect to the vanadium only under very acidic pH conditions, of markedly less than 1, that is to say when the metal compounds are present in a concentrated nitric acid solution, for example.

SUMMARY OF THE INVENTION

One of the aims of the present invention is to provide a novel process which makes it possible to selectively separate the iron from other metal ions, in particular from the vanadium ions, and thus to provide a very efficient process for the recycling of the catalyst for the oxidation of organic compounds, more particularly of alcohols and/or of ketones to carboxylic acids and more preferably still of cyclohexanol and/or cyclohexanone to adipic acid.

To this end, the invention provides a process for selectively separating the iron present in a solution in the presence of other metal ions, including vanadium. These solutions are generally solutions originating from processes for the oxidation of an organic compound in the presence of a vanadium-based catalyst.

According to the characteristic of the invention, the solution comprising the said metal ions is treated with an ion-exchange resin comprising diphosphonic acid groups.

During this treatment, the iron is fixed by the resin; the metal ions, such as, in particular, copper and vanadium, remain in the treated solution.

The process of the invention makes it possible to fix to the resin at least 80% of the iron present in the solution.

According to another characteristic of the invention, the solution to be treated comprising the metal ions has a very low pH, advantageously of less than 3 and of preferably less than 2.

According to a preferred characteristic of the invention, the ion-exchange resin also comprises sulphonic groups.

The use of resins comprising diphosphonic acid groups and optionally sulphonic groups makes it possible, in a noteworthy way, to fix the iron present in a solution without fixing other metal cations, such as copper and more particularly vanadium.

This process applies more particularly to the recycling of the catalysts in reactions for the oxidation of organic compounds and more particularly of alcohols and/or ketones to carboxylic acids. Such an oxidation process also constitutes a subject-matter of the present invention.

This is because, in these processes, the iron is often a contaminating element originating mainly from corrosive attack on the equipment by the oxidation medium.

Mention may be made, as oxidation reactions in which the process of the invention makes possible efficient recycling of the catalyst, of oxidation reactions using, as oxidizing agent, a compound chosen from the group consisting of oxygen, air, peroxides, aqueous hydrogen peroxide solution and nitric acid.

Mention may be made, as example of oxidation reaction, of the reaction for the deperoxidation of cyclohexane hydroperoxide.

It applies in particular in the process for the manufacture of adipic acid from the oxidation of cyclohexanol and/or cyclohexanone, which process is also a subject-matter of the present invention.

In such processes, it is important from an economic viewpoint, and to avoid discharge of metals to the environment, to recycle the catalyst comprising metal elements, such as, for example, copper and/or vanadium, while minimizing the bleeds or the flow of unrecycled catalyst.

However, in order for such a recycling process not to disturb the oxidation reaction, it is necessary to avoid the recycling or the concentration of certain products or byproducts which have a poisoning effect on the catalyst or which can contaminate the products manufactured.

In the case of the manufacture of adipic acid by oxidation of cyclohexanol and/or cyclohexanone with an oxidant such as nitric acid, corrosion of the plants results in particular in the presence of iron in the reaction mixture.

It is consequently important for the functioning of the process to provide for the removal of the iron. This removal must be obtained without removal of the other metal ions used as catalyst for the oxidation, such as copper and vanadium.

The process of the invention makes it possible to carry out this removal of the iron by treatment of the solution comprising the various metal ions recovered after separation of the organic compounds and in particular of the carboxylic acid or acids formed.

This removal of the iron is obtained by treatment of the said solution with an ion-exchange resin comprising diphosphonic acid groups and optionally sulphonic groups.

After treatment, the solution comprises the metal ions with the exception of iron ions, the latter being fixed to the resin. The amount fixed is advantageously greater than 80% of the amount initially present in the solution.

Thus, the process of the invention makes it possible to recycle a solution comprising the metal ions of use in the catalysis with a minimum loss of the said ions and an absence of the iron ions or a presence of the latter at a very low and untroublesome concentration.

Thus, in the case of the manufacture of adipic acid by oxidation of an alcohol and/or a ketone by nitric acid, the treatment of the aqueous solution comprising the metal ions originating from the oxidation catalyst, namely, preferentially, vanadium and copper, with an ion-exchange resin comprising diphosphonic groups and optionally sulphonic groups makes it possible to remove the iron originating in particular from the corrosion of the plants and to recycle a catalytic solution with a minimum loss of catalytic elements, in particular of vanadium and of copper.

In addition, as the concentration of iron in the reaction mixture is maintained at a very low level, the process of the invention makes possible production of adipic acid with a very low, indeed even zero, content of iron.

BRIEF DESCRIPTION OF THE FIGURES OF THE DRAWINGS

FIG. 1 is a graph showing the percentage of metal ions fixed to ion-exchange resin in the process of Example 1;

FIG. 2 is a graph showing the percentage of metal ions fixed to ion-exchange resin S940 in Comparative Example 2;

FIG. 3 is a graph showing the percentage of metal ions fixed to ion-exchange resin C467 in Comparative Example 3.

FIG. 4 is a graph showing the percentage of metal ions fixed to ion-exchange resin Eichrom Diphonix® in Example 4;

FIG. 5 is a graph showing the percentage of metal ions fixed to ion-exchange resin Purolite S-940 in Comparative Example 5; and FIG. 6 is a graph showing the percentage of metal ions fixed to ion-exchange resin C467 in Comparative Example 6.

DETAILED DESCRIPTION OF THE PREFERRED EMBODIMENTS

The treatment of the solution is carried out, in a first embodiment, after extraction of the adipic acid and optionally separation of the precipitated vanadium.

The solution, purified of iron, can subsequently be treated with a second ion-exchange resin which fixes all the metal ions, in order to avoid recycling a solution comprising organic byproducts from the oxidation reaction, such as glutaric acid and/or succinic acid. The recycled catalytic solution is composed of the solution from the elution of the said resin, which solution is generally composed of a nitric acid solution.

In a second embodiment, the treatment on an ion-exchange resin comprising diphosphonic acid groups and optionally comprising sulphonic groups can be carried out on the solution from the elution of the resin which makes it possible to separate the organic byproducts from the metal ions which are described above.

According to another characteristic of the invention, the ion-exchange resin comprising diphosphonic groups and optionally comprising sulphonic groups is regenerated by elution with an inorganic acid solution. Mention may be made, as suitable inorganic acids, of nitric acid, phosphoric acid or sulphuric acid.

Preferably, it is preferable to use an acid identical to that used to prepare the catalytic oxidation solution, generally nitric acid, in order thus to avoid contamination of the reaction mixture by another acid.

However, it is possible to regenerate the resin with a different acid and then to condition the resin with the acid identical to that of the catalytic solution, for example nitric acid, before a fresh use. It is also possible to carry out this conditioning by washing the resin with water several times in order to remove the traces of elution acid.

The conditions for carrying out the treatment on an ion-exchange resin in accordance with the invention are the conventional conditions for the use of resins. Thus, the temperature for carrying out this treatment can vary from room temperature (approximately 20° C.) to a temperature of approximately 100° C., preferably between 30° C. and 80° C.

Likewise, the concentration of the acidic regeneration solution is conventional. It can, for example, be between 10% and 40% by weight.

The ion-exchange resins in accordance with the invention comprising diphosphonic acid groups and optionally sulphonic groups are, for example, those disclosed in U.S. Pat. Nos. 5,449,462 and 5,281,631.

These resins are obtained by polymerization of various monomers, some of which comprise diphosphonic acid groups. The resin can be a polystyrene resin with diphosphonic groups.

The resin can also comprise carboxylic groups and/or sulphonic groups.

The processes for the manufacture of these resins are disclosed in the two abovementioned United States patents. The description of their structures is also given in these documents.

These resins are sold in particular by the company Eichrom Industries under the tradename Eichrom Diphonix®.

Other advantages and details of the invention will become apparent in the light of the examples given hereinbelow solely by way of indication.

EXAMPLE 1

600 ml of an aqueous solution comprising 1.3% of nitric acid, 10,485 ppm of copper ion, 1353 ppm of iron ion and 281 ppm of vanadium ion are introduced into a receptacle.

50 ml of ion-exchange resin sold under the name Eichrom Diphonix® are added.

The mixture is stirred for variable times.

The concentration of metals in the solution is measured after being brought into contact for variable periods of time.

The percentage of metal fixed to the resin as a function of the duration of treatment is represented in graph 1.

It is easily observed from this graph that the iron is virtually completely fixed to the resin. In contrast, small amounts of vanadium and of copper are fixed at the beginning of the operation, these amounts remaining constant throughout the operation.

The treatment thus makes possible selective separation of the iron from the other metal ions and in particular from the vanadium.

COMPARATIVE EXAMPLES 2 AND 3

Similar tests were carried out with ion-exchange resins comprising aminophosphonic groups in accordance with European Patent 0,761,636.

The two resins used are respectively a resin sold under the name Purolite S-940 and a resin sold by the company Röhm & Haas under the tradename C467.

The percentage of metal ions fixed as a function of the duration of treatment is represented in graphs 2 and 3 for the resin S940 and C467 respectively.

As may be observed, these resins fix at most 60% of the iron present in the solution but, above all, fix virtually all the vanadium.

Consequently, these resins, used in processes for recycling vanadium-based oxidation catalysts, have a major disadvantage.

In addition, they do not make it possible to carry out the selective separation of the iron with respect to the vanadium.

EXAMPLES 4, 5c AND 6c

Example 1 is repeated on a solution comprising 19.9% of nitric acid, 8875 ppm of copper, 1192 ppm of iron and 165 ppm of vanadium.

This solution corresponds to the solution of eluates with nitric acid of a cation-exchange resin on which has been treated a solution originating from a process for the oxidation of cyclohexanol with nitric acid.

The results obtained with an Eichrom Diphonix® resin, the Purolite S-940 resin and the Röhm & Haas C467 resin are represented respectively by the graphs 4, 5 and 6.

As in the preceding examples, the resin in accordance with the invention makes it possible to fix a large amount of iron (at least 60% of the starting amount) while fixing a minimum of the other vanadium and copper cations.

In contrast, the other two resins fix a significant amount of vanadium simultaneously with the iron.

EXAMPLE 7

Regeneration of the Eichrom Diphonix® resin

The resins, laden with iron, obtained in Examples 1 and 4 are regenerated by elution with various acidic solutions by passing 100 ml of elution solution through 10 ml of resin.

The results obtained are collated in the following table. These results represent the percentage of metal ions which are recovered by the elution with respect to the amount fixed.

|  | Resin, Example 1 | | | Resin, Example 4 | | |
| --- | --- | --- | --- | --- | --- | --- |
|  | Cu | Fe | V | Cu | Fe | V |
| $HNO_3$ | 95 | 29 | 97 | 52 | 14 | 56 |
| $H_2SO_4$ | 91 | 35 | 95 | 50 | 21 | 53 |
| $H_3PO_4$ | 87 | 50 | 90 | 45 | 37 | 50 |

The invention claimed is:

1. A process for the manufacture of adipic acid by oxidation of cyclohexanol and/or cyclohexanone in the presence of a catalyst based on metal elements, which comprises treating a solution resulting from the oxidation, said solution comprising the catalyst, after separation of the adipic acid formed, with at least one ion-exchange resin comprising diphosphonic groups, in order to selectively remove from said solution iron ions present therein, and reusing said treated solution as a catalyst for the oxidation.

2. The process according to claim 1, wherein said catalyst is based on copper and vanadium.

3. The process according to claim 1 wherein the solution comprising the catalyst is a nitric acid solution.

4. A process according to claim 1, wherein the ion-exchange resin comprising diphosphonic acid groups is regenerated with an acidic solution.

5. The process according to claim 4, wherein the regeneration of the resin is carried out with a different acid from nitric acid and the said regenerated resin is conditioned with a nitric acid solution or by washing with water before a fresh use.

6. A process for the manufacture of adipic acid by oxidation of cyclohexanol and/or cyclohexanone in the presence of a catalyst based on metal elements, which comprises:
  (1) treating a solution resulting from the oxidation, said solution comprising the catalyst, after separation of the adipic acid formed, with at least one ion-exchange resin comprising diphosphonic groups in order to selectively remove from said solution iron ions present therein;
  (2) contacting the treated catalyst-containing solution from step (1) with an ion-exchange resin to selectively remove said metal elements of the catalyst;
  (3) treating the ion-exchange resin in step (2) to form an eluate solution containing said metal elements; and
  (4) reusing said eluate solution as a catalyst for said oxidation.

* * * * *